United States Patent [19]

Kano

[11] 4,447,396
[45] May 8, 1984

[54] SYSTEM FOR DISCRIMINATING A PRECIPITATION PATTERN OF PARTICLES

[75] Inventor: Tokio Kano, Tokyo, Japan

[73] Assignee: Olympus Optical Co., Ltd., Tokyo, Japan

[21] Appl. No.: 337,068

[22] Filed: Jan. 4, 1982

[51] Int. Cl.³ .................... G01N 33/54; G01N 35/02
[52] U.S. Cl. .................................. 422/73; 356/343; 356/442; 422/67
[58] Field of Search ............... 364/497, 498; 422/73, 422/64, 67; 356/343, 442, 446

[56] References Cited

U.S. PATENT DOCUMENTS

| | | | |
|---|---|---|---|
| 4,139,303 | 2/1979 | Carlsson et al. | 356/39 |
| 4,341,471 | 7/1982 | Hogg et al. | 356/343 |

FOREIGN PATENT DOCUMENTS

| | | | |
|---|---|---|---|
| 3033870 | 4/1981 | Fed. Rep. of Germany | 422/73 |
| 56-2560 | 1/1981 | Japan | 422/73 |

*Primary Examiner*—Michael S. Marcus

[57] ABSTRACT

A system for discriminating a precipitation pattern of particles comprises a transparent reaction container which has an inverted conical bottom surface. The precipitation pattern of particles of agglutination, non-agglutination and intermediate state between the agglutination and the non-agglutination are formed based on the immunologic agglutination on the bottom surface of the reaction container. The image of the precipitation pattern is projected through a lens to the electric converting element. A first photodetector is disposed at the center of the image projected on the surface of the photoelectric transducer element, four second photodetectors are disposed around the center of the image, and further five third photodetectors are disposed around the second photodetectors. A first detection signal which correspond to the difference of the outputs from the first detector and the one of third detectors is generated from a first subtracting unit. The outputs of the first and the second detectors are added, the outputs from the third detectors are similarly added, and the difference of the added signal is generated as the second detection signal from a second subtracting unit. The first and the second detection signals are compared by the discriminating unit to discriminate whether or not it is agglutination, non-agglutination or intermediate state between the agglutination and the non-agglutination.

9 Claims, 13 Drawing Figures

SYSTEM FOR DISCRIMINATING A PRECIPITATION PATTERN OF PARTICLES

BACKGROUND OF THE INVENTION

I. Field of the Invention

The present invention relates to a system for discriminating a precipitation pattern of particles formed based on immunological agglutination and, more particularly, to a system for grouping or testing blood or discriminating an antibody and an antigen based on immunological agglutination.

II. Description of the Prior Art

A method of grouping blood from a precipitation pattern of blood corpuscles is already disclosed in Japanese Patent Publication No. 51-16798 (16798/1976). According to the blood grouping method, blood corpuscles to be inspected are separated by centrifugation. These blood corpuscles are recovered to prepare a 2 to 5% blood corpuscle suspension. This suspension and an antiserum are poured in appropriate quantities in a wine-cup-shaped reaction container. The container is then shaken, and allowed to stand. Thereafter, reaction mixture in the reaction container is subjected to centrifugation. The reaction containers are then relatively vigorously shaken, and subsequently relatively slowly shaken so that the reacted or agglutinated corpuscles are collected at the center region on the bottom of the containers. As a result, the precipitation pattern based on the agglutination of the blood corpuscles is formed on the bottom surface of the container. The precipitation pattern thus formed includes agglutination pattern and non-agglutination pattern. The agglutination pattern is formed as a result that the blood corpuscles are agglutinated with the antiserum and collected at the center region on the bottom surface of the reaction container. The non-agglutination pattern is formed as a result that agglutination does not occur, the blood corpuscles not agglutinated are dispersed in suspension. Accordingly, discrimination can be made on whether or not agglutination occurs by measuring the precipitation pattern optically.

The aforementioned blood grouping method is utilized exclusively for the ABO blood grouping since it includes the step of vigorously shaking the reaction container. The natural antibody used in this method agglutinates the blood corpuscles with large agglutinating force, and the agglutinated blood corpuscles are not separated from each other during such shaking step.

However, this method cannot be adopted for immunological method in which a reactant having a weak agglutinating force is involved a method of examining a variety of irregular antibodies, antigens or HBs antigens or the like. More specifically, if the agglutinating force is weak, when the reaction container is shaken, the blood corpuscles which have once agglutinated become separated from each other, and are not collected at the center of the reaction container.

Therefore, a method of employing a microplate with a number of small reaction containers or holes each having an inverted conical bottom surface is adopted for detection and grouping of the HBs antigens. This method, for example, detects and examines the HBs antigens with the steps described below, using, for example, a microplate having 10×12 pores.

(1) Droplets (each having a volume of 0.025 ml) of R-PHA buffer solution are added one by one to the respective holes of the microplate.

(2) A sample is diluted twice with a diluter, and ten types of samples having different dilution degrees are thus obtained. Two rows of such samples having different dilution degrees are prepared.

(3) One droplet of R-PHA buffer solution is added to the one row of the diluted samples, and one droplet (having a volume of 0.025 ml) of R-PHA inhibition solution is added to the other row of the diluted samples.

(4) After the solution in each hole is sufficiently shaked with a micromixer for 10 seconds, it is incubated at 37° C. for 1 hour.

(5) One droplet (having a volume of 0.025 ml) of a 1% R-PHA cell floating liquid is added to each hole.

(6) The solution in each hole is sufficiently shaked with the micromixer for 10 seconds, and the R-PHA cell is uniformly suspended.

(7) After it is left to stand for 1 hour, avoiding shaking, at room temperature, the pattern formed on the bottom surface of each hole is examined.

According to this detecting method, since the microplate is sufficiently left to stand without shaking immediately before the detection, the agglutinated sample may not be separated, and the precipitation pattern based on immunological agglutination involving a reactant having relatively weak agglutinating tendency can be accurately formed on the bottom of each pore.

The inventor of the present invention has proposed as one of joint inventors in Japanese Patent Application No. 54-53370 a blood group detecting method which can sufficiently detect blood group based on immunological agglutinations involving natural antibody having strong agglutinating tendency and also can detect irregular antibody having weak agglutinating tendency. According to this blood group detecting method, blood corpuscles and reference antiserum reagent are contained in a reaction container having, for example, an inverted conical bottom surface, agitated, left to stand for a relatively short time (such as for approx. 30 minutes), and precipitation pattern is then examined to discriminate the blood group. According to this method, when the blood corpuscles to be examined react with the antiserum reagent, the precipitated blood corpuscles are thinly accumulated like snow on the inverted conical bottom as the blood corpuscles are agglutinated, and uniformly accumulated agglutination pattern is formed. When the blood corpuscles do not react with the antiserum reagent, the blood corpuscles do not agglutinate, but precipitate. When the blood corpuscles reach the inverted conical bottom, the blood corpuscles fall down along the oblique surface of the inverted conical bottom to collect at the center of the conical bottom surface, and non-agglutination pattern is formed. Accordingly, the blood group can be examined by photoelectrically detecting the difference of the precipitation pattern of the blood corpuscles formed depending upon whether or not the blood corpuscles react with the antiserum reagent.

However, the aforementioned various precipitation pattern discriminating methods fails to accurately detect the precipitating pattern formed on the bottom of the reaction container. According, for example, to the method disclosed in Japanese Patent Publication No. 51-16798 employing the wine-cup-shaped reaction container, the turbidity of the solution in the reaction container is measured by detecting the brightness of light passing through the reaction solution. That is, when the light beam passes through the solution, the degree of absorption of the light varies depending upon the amount of the blood corpuscles present in the path of the light beam, and the transmitted light beam is photoelectrically measured. In the embodiment shown in FIG. 33 of the Japanese Patent Publication No. 51-16798, light is incident from the top of the wine-cup-shaped reaction container. A mask having a center opening and an annular opening surrounding the center opening is disposed at the lower part of the reaction container, the light passed through the center opening is incident to the first photodetector, and the light passed through the annular opening is incident through a lens to the second photodetector. Accordingly, the brightness of light passed through the center of the reaction solution in the reaction container into the first photodetector represents the turbidity of the center region of the reaction solution, and the brightness of light passed through the periphery of the reaction solution incident to the second photodetector represents the turbidity of the periphery region of the reaction solution. Therefore, when the brightness of light passed through the center of the reaction solution is reduced than the reference value and the brightness of light passed through the periphery of the reaction solution is increased than the reference value, this is examined as "agglutination". When the brightness of light passed through the center and the periphery of the reaction solution does not change with respect to the reference value, it is examined as "non-agglutination". This precipitation pattern detecting method is considered to have no problem in case that the distance from the bottom surface of the reaction container to the center opening of the mask is shorter than the lateral expansion of the precipitation pattern. If the distance from the bottom surface to the center opening is longer than the lateral expansion, the light incident to the periphery of the reaction solution is scattered by the particles, tends to be incident through the periphery of the reaction solution to the first photodetector and the light incident to the center is scattered by the particles, and accordingly the brightness of light incident through the annular opening to the second photodetector is increased, with the result that an accurate light measurement cannot be conducted disadvantageously. More particularly, in case that it is impossible to dispose the opened mask sufficiently near at the bottom of the reaction container due to the system arrangement, or in case that the mask cannot be disposed sufficiently near at the reaction solution due to the necessity of irradiating the light from the bottom of the container and receiving the light from the top of the container, the light scattered with the particles in the reaction solution reduces the measuring accuracy to thus cause impossibility in the accurate examination. In order to eliminate such disadvantages, it is considered to increase the size of the reaction container so as to increase the difference of the turbidity of the solution. In this case, the quantity of sample is increased, and the sample cannot be substantially analyzed. An optical detecting system should be considerably complicated in order to obtain an accurate discrimination. Particularly when it is necessary to adopt a small reaction container so as to reduce the quantity of sample, it is difficult to decrease the size of the optical detecting system to thus cause a difficulty in the production and adjustment thereof.

Further, if the aforementioned turbidity measuring method is employed for the discriminating method disclosed in Japanese Patent Application No. 54-53370, the measuring accuracy cannot be raised. Particularly when the agglutination pattern and the non-agglutination pattern are automatically detected and discriminated, it needs a detecting equipment having considerably high accuracy. Moreover, the precipitation pattern formed on the bottom surface of the reaction container is not so always formed as to be distinct to be capable of distinguished from each other, and the intermediate state between the agglutination pattern and non-agglutination pattern may also be formed. It is necessary to examine the precipitation pattern including the intermediate pattern by accurately reading the precipitation pattern.

SUMMARY OF THE INVENTION

It is an object of the present invention to provide a system for accurately discriminating precipitation pattern of particles formed by immunological agglutination.

It is another object of the present invention to provide a system for accurately discriminating whether precipitation pattern of particles formed by immunological agglutination corresponds to agglutination pattern, non-agglutination pattern or the intermediate pattern between the agglutination pattern and the non-agglutination pattern.

According to the present invention, there is provided a system for discriminating whether the precipitation pattern of particles formed in a reaction container corresponds to an agglutination, a non-agglutination and an intermediate state between the agglutination and the non-agglutination based on the immunological agglutination. The image of the precipitation pattern on the bottom surface of the reaction container is projected through a lens to the surface of a photodetector. The photodetector includes at least of first, second and third photoelectric converting elements, and the photodetecting surfaces of the elements are respectively disposed on regions having different brightness of pattern images. The difference between outputs from the first and the third photoelectric elements is generated as the first detection signal. The difference of one of the outputs from the first and the third photoelectric elements and the output of the second photoelectric element is generated as the second detection signal. The agglutination, non-agglutination or the intermediate state between the agglutination and the non-agglutination is discriminated by the first and the second detection signals.

DETAILED DESCRIPTION OF THE PREFERRED EMBODIMENTS

The present invention will now be described in more detail with reference to the accompanying drawings.

Figure 1:
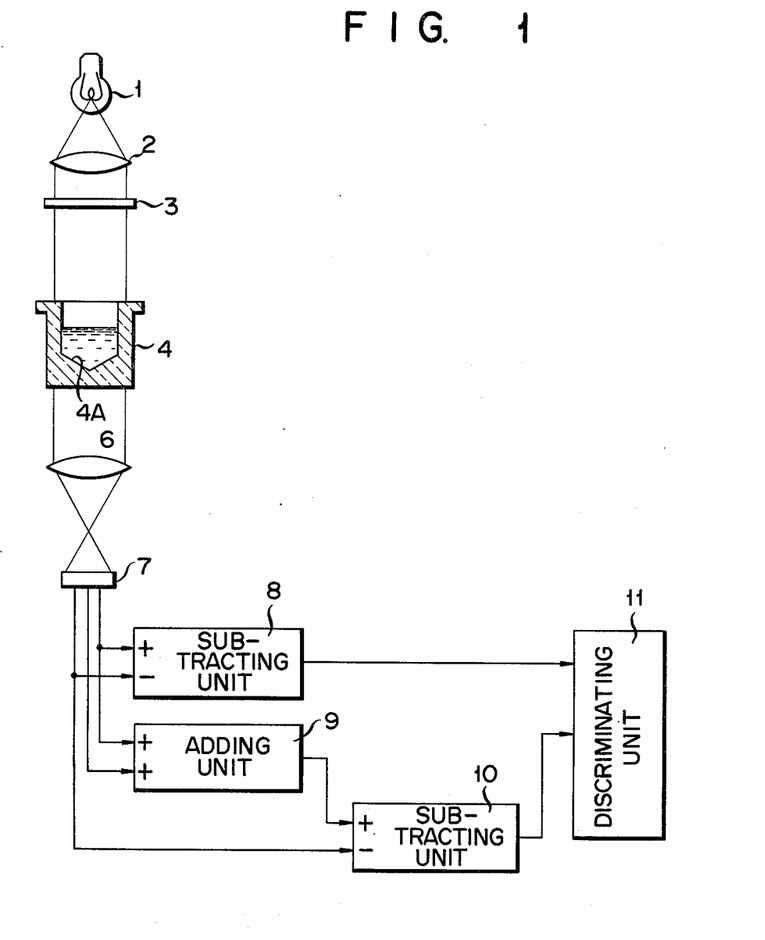
FIG. 1 is a block diagram showing a system for discriminating a precipitation pattern of particles according to one preferred embodiment of the present invention.
Figure 2A:
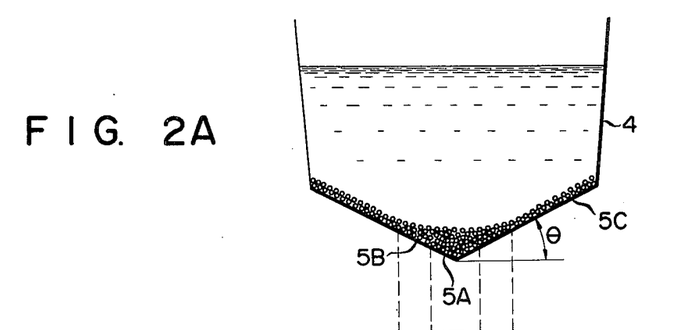
FIG. 2A is a sectional view showing schematically a reaction container in the system shown in FIG. 1.
Figure 2B:
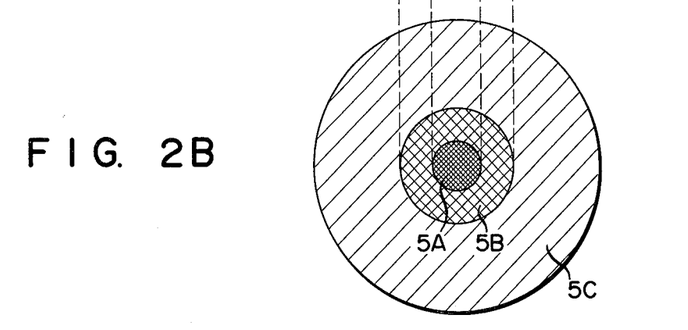
FIG. 2B is a plan view showing schematically a photodetector in the system shown in FIG. 1.

FIG. 1 is a block diagram showing one preferred embodiment of the system for discriminating a precipitation pattern of particles according to the present invention. Light emitted from a light source 1 is converted into parallel beams by a collimator lens 2, and the beams are projected by a projection lens of greater depth of focus through a diffusing plate 3 to a transparent reaction container 4. The reaction container 4 is uniformly illuminated by the diffused light. The reaction container 4 has, as may be seen from the expanded view in FIG. 2A, a substantially inverted conical bottom, which has, for example, approx. 6 mm of radius and approx. 1.5 mm of the depth of the inverted conical part with the oblique angle $\theta$ with respect to the horizontal line being preferably 25 to 30°. FIG. 2A shows the precipitation pattern of the agglutinated particles formed uniformly on the inverted conical bottom. The agglutinated pattern is formed, for example, when anti-A antiserum reagent is added to A type blood corpuscle. That is, when the agglutination occurs, the blood corpuscles are precipitated while agglutinating by allowing them to stand to reach the bottom surface of the container, almost without falling down along the oblique surface of the inverted conical bottom of the container. Accordingly, the blood corpuscles are substantially uniformly accumulated on the bottom surface. When observed in detail, in the precipitated pattern layer, the blood corpuscles are accumulated relatively thickly on the lowermost region 5A at the center of the bottom surface, but accumulated thinly on the peripheral region 5C, and the pattern layer continuously varies in thickness at the intermediate region 5B between the center and the peripheral region of the bottom of the container (FIG. 2B).

The precipitation pattern thus formed on the bottom 4A of the reaction container 4 is focused on a photoelectric transducer element 7, and the image of the pattern is formed on the electric transducer element 7.

Figure 3:
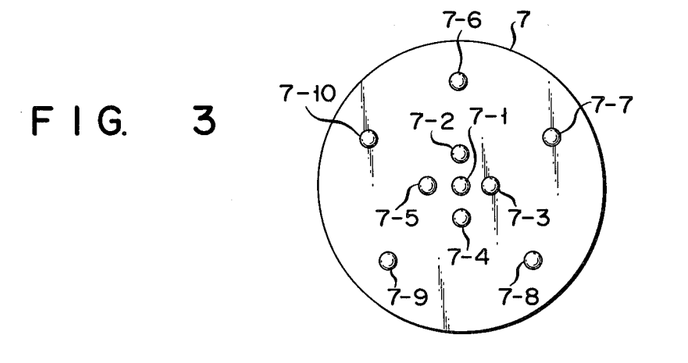
FIG. 3 is a schematic plan view of the photodetector arrangement of photoelectric transducer element in the system shown in FIG. 1.

The electric transducer element 7 comprises, as may be seen from the plan view in FIG. 3, first to tenth photodetectors 7-1 to 7-10. The photodetecting surface of the first photodetector 7-1 is disposed at the central axis of the system, and an image of the central region 5A of the agglutination pattern having lower brightness than the other regions is projected to the photodetecting surface of the first photodetector 7-1. The photodetecting surfaces of the second to fourth photodetectors 7-2 to 7-4 are disposed around the photodetecting surface of the first photodetector 7-1, and the image of the middle region 5B of the agglutination pattern having higher brightness than the central region is projected to the photodetecting surfaces of the second to fourth photodetectors. The photodetecting surfaces of the sixth to tenth photodetectors 7-6 to 7-10 are disposed at further outer regions thereof, and the image of the peripheral region 5C of the agglutination pattern having higher brightness than the central region and the intermediate peripheral region is projected to the photodetecting surfaces of the sixth to tenth photodetectors.

As shown in FIG. 1, the outputs from the first photodetector 7-1 and from one of the sixth to tenth photodetectors, for example, the sixth photodetector 7-6 are supplied to the first subtracting unit 8, which thus obtains the difference therebetween. The outputs from the first and the second to sixth photodetectors 7-1 to 7-10 are supplied to an adding unit 9, the output of which is supplied to one input terminal of the second subtracting unit 10. To the other input terminal of the second subtracting unit 10 is supplied the sum of the outputs from the sixth to tenth photodetectors 7-6 to 7-10. The outputs from the first and the second subtracting units 8 and 10 are supplied to a discriminating unit 11, which thus discriminates the precipitation pattern. The discriminated result of the discriminating unit 11 is printed or visually indicated.

Figure 4:
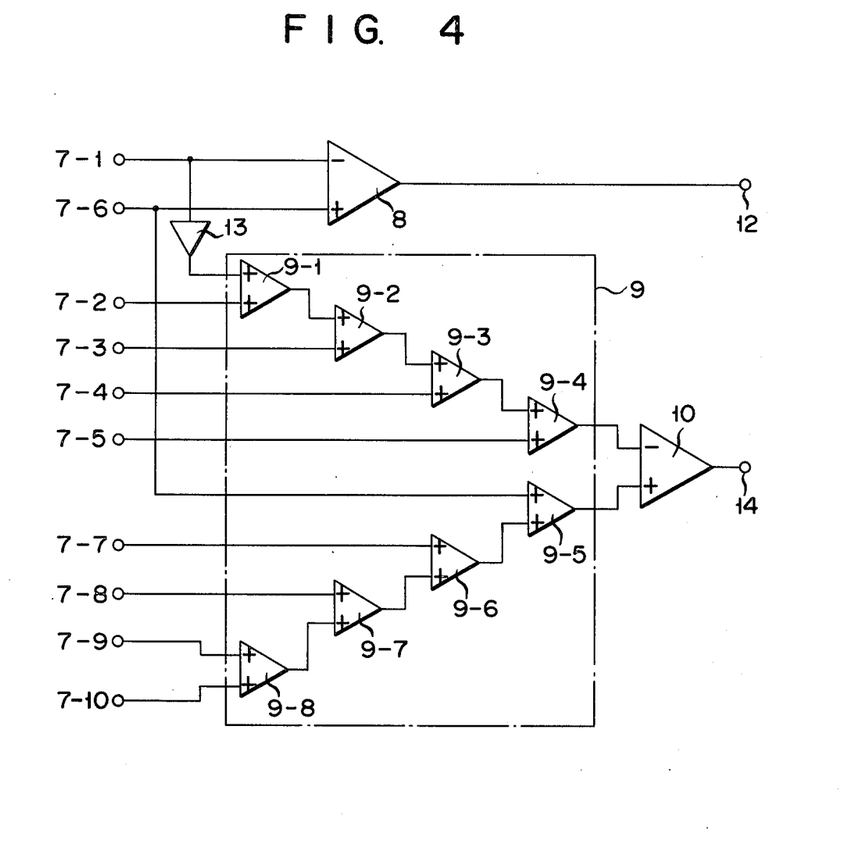
FIG. 4 is a circuit diagram showing subtracting and adding units in the system shown in FIG. 1.

FIG. 4 is a circuit diagram showing the first and the second subtracting units 8 and 10 and the adding unit 9. The subtracting unit 8 is formed of a differential amplifier, and subtracts the output from the first photodetector 7-1 from the output from the sixth photodetector 7-6, and produces a subtraction output to an output terminal 12. The adding unit 9 comprises a plurality of analog adders 9-1 to 9-8. To the adder 9-1 is supplied through an amplifier 13 the output from the first photodetector 7-1, and to the adders 9-1 to 9-8 are supplied the outputs from the photodetectors 7-2 to 7-10. The amplifier 13 is provided to match the level of the output signal from the first photodetector 7-1 to the level of the outputs from the photodetectors 7-2 to 7-5 of the intermediate region 5B substantially in the same level. Thus, the total sum of the outputs of the photodetectors 7-1 to 7-5 is outputted from the output terminal of the adder 9-4, the total sum of the outputs of the photodetectors 7-6 to 7-10 is outputted from the output terminal of the adder 9-5, the these outputs of the adders 9-4 and 9-5 are supplied to the second subtracting unit 10 which is formed of a differential amplifier, and which thus produces the compared output to an output terminal 14.

Figure 5A:
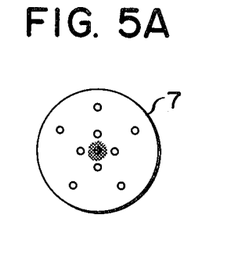
FIGS. 5A through 5C are respectively plan views showing schematically the images of the non-agglutination, intermediate and agglutination patterns projected to the photodetectors.
Figure 5B:
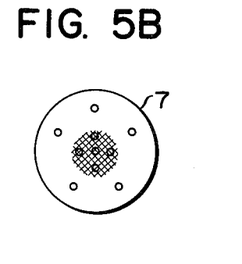
Figure 5C:
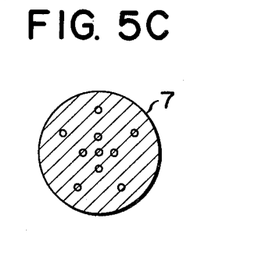

FIGS. 5A, 5B and 5C show schematic precipitation patterns formed on the bottom 4A of the reaction container 4. FIG. 5A shows the non-agglutination pattern in which agglutination does not occur and the precipitated particles roll down on the oblique surface of the bottom of the container to be thus accumulated in the vicinity of the center on the bottom. FIG. 5C shows the agglutination pattern formed by the agglutination as indicated in FIGS. 2A and 2B, and FIG. 5B shows the intermediate state between the agglutination pattern and the non-agglutination pattern, which will be hereinafter called "an intermediate pattern". According to the present invention such various patterns can be accurately discriminated. The following Table I shows detection signals presented at the output terminals 12 and 14 for the respective patterns shown in FIGS. 5A through 5C. In the Table I, the respective photodetectors produce outputs of high level when the image is bright and hence when the accumulated particles is less.

TABLE I

| Patterns | Outputs | | Discrimination |
| --- | --- | --- | --- |
| | Output terminal 12 | Output terminal 14 | |
| Non-agglutination pattern in FIG. 5A | + | 0 | Non-agglutination |
| Intermediate pattern in FIG. 5B | + | + | Intermediate state |
| Agglutination pattern in FIG. 5C | 0 | − | Agglutination |

Figure 6:
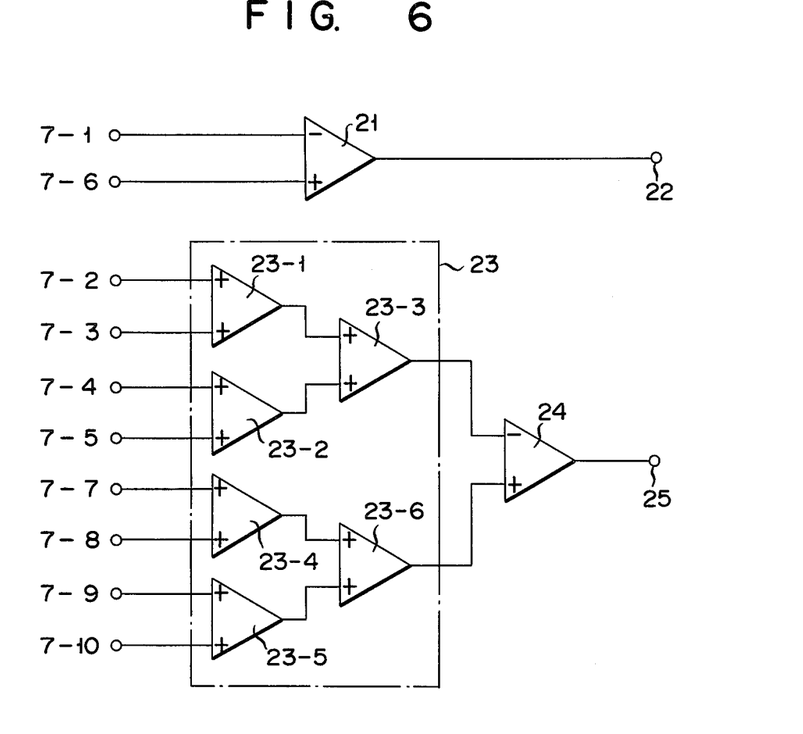
FIG. 6 is another circuit diagram of the subtracting and adding unit in the system shown in FIG. 1.

FIG. 6 shows a circuit diagram showing another circuit of the subtracting and adding unit for executing the agglutination pattern discriminating method. The electric transducer element used in this example is constructed in the same manner as that in the previous embodiment and comprises ten photodetectors 7-1 to 7-10 arranged as shown in FIG. 3. The outputs from the first and the sixth photodetectors 7-1 and 7-6 are supplied to the first differential amplifier 21, which produces a compared output to an output terminal 22. The outputs from the second to fifth photodetectors are added by analog adders 23-1 to 23-3 of an adding unit 23, the output from the adders 23-3 is supplied to one input terminal of the second differential amplifier 24. The outputs from the seventh to tenth photodetectors are added by analog adders 23-4 to 23-6 of the adding unit 23, the output from the adder 23-6 is supplied to the other terminal of the second differential amplifier 24. The compared output from the differential amplifier 24 is supplied to an output terminal 25.

In this embodiment, the detection output signals shown in the following Table II are obtained at the output terminals 22 and 25 correspondingly to the patterns shown in FIGS. 5A to 5C, and the respective patterns can be thus accurately discriminated.

TABLE II

| Patterns | Outputs | | Discrimination |
| --- | --- | --- | --- |
| | Output terminal 22 | Output terminal 25 | |
| Non-agglutination pattern in FIG. 5A | + | 0 | Non-agglutination |
| Intermediate pattern in FIG. 5B | + | + | Intermediate state |
| Agglutination pattern in FIG. 5C | 0 | − | Agglutination |

Figure 7:
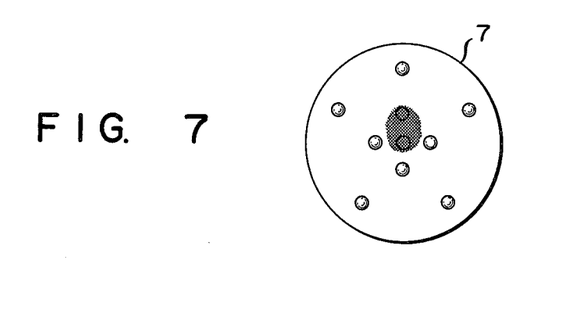
FIG. 7 is a schematic plan view in which the image of the non-agglutination pattern is displaced from the center of the photodetector.
Figure 8:
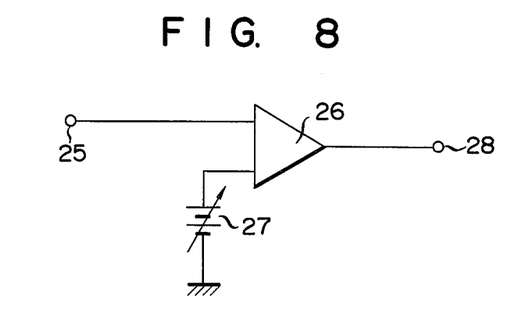
FIG. 8 is a circuit diagram showing an example of the circuit for correcting the output of the subtracting unit when the image is displaced as shown in FIG. 7.

The various patterns are formed around the center of the oblique bottom of the reaction container, and the image is accurately focused on the electric transducer element in the foregoing description. If the accuracy of the reaction container is actually wrong or if there is an error in the alignment of the optical system, the center of the precipitation pattern may be displaced from the center of the electric transducer element as shown in FIG. 7. In this case, when the precipitation pattern is changed from the non-agglutination pattern shown in FIG. 5A to the intermediate pattern shown in FIG. 5B, the output signal from the output terminal 25 varies relatively small, thereby the precipitation pattern may not be accurately discriminated. In order to eliminate such drawback, the output terminal 25 is connected to one input terminal of a comparator 26 as shown in FIG. 8, and to the other input terminal of the comparator 26 is applied a reference voltage from a reference voltage source 27. When the value of the reference voltage is set at a predetermined value between the output obtained when the non-agglutination pattern is obtained and the output obtained when the intermediate pattern is obtained, any of "0 or −" and "+" can be obtained as the clearly different output between the non-agglutination pattern and the intermediate pattern at the output terminal 28 of the comparator 26.

Figure 9:
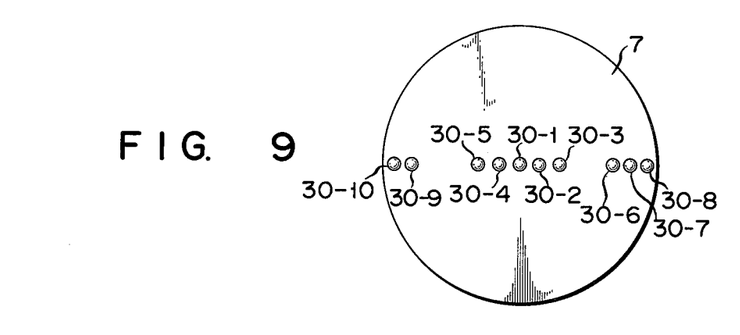
FIGS. 9 and 10 are schematic plan views of the photodetector arrangement in the photodetector.
Figure 10:
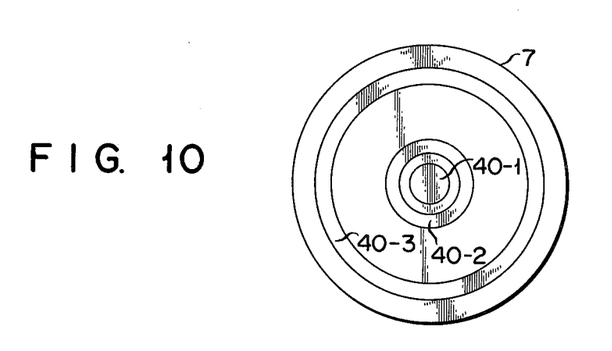

The present invention is not limited to the particular embodiments described above. Various other changes and modifications may be made within the spirit and scope of the present invention. For example, in the array of the photodetectors in the electric transducer element, various arrays can be employed. As shown in FIG. 9, the array may also include the arrangement such that the photodetecting surface of one photodetector 30-1 is disposed at the center, the photodetecting surfaces of two photodetectors 3-2 to 3-5 are disposed at both sides of the center photodetector 30-1, and the photodetecting surfaces of three photodetectors 30-6 to 30-8 and two photodetectors 30-9 and 30-10 are respectively disposed at both sides of the outsides of the photodetectors 3-2 to 3-5. In the embodiments described above, at least one photodetectors for receiving the image of the center 5A of the precipitation pattern may be provided, and at least one photodetector for receiving the image of the intermediate region 5B in the vicinity of the image of the center region 5A may be provided, and at least two photodetectors for receiving the image of the peripheral region 5C may be provided. Moreover, as shown in FIG. 10, three photodetectors 40-1, 40-2 and 40-3 may be coaxially arranged at the respective photodetecting surfaces without using the respective photodetectors. It is also noted that the foregoing description is directed to the arrangement that the bottom surface of the reaction container is formed conically, but the bottom surface of the reaction container may also be formed in a lean-to shape, gable roof shape, pyramid shape and so forth. In addition, it is also noted that the foregoing description is directed to the arrangement that the light passed through the precipitation pattern is projected to the electric transducer element 7 as shown in FIG. 1, but the light reflected from the precipitation pattern may also be projected thereto. That is, the light source 1 may also be disposed to illuminate the bottom surface of the reaction container.

According to the present invention, the precipitation pattern may be clearly discriminated whether or not it corresponds to any of the agglutination pattern, non-agglutination pattern and the intermediate pattern therebetween. Accordingly, the system of the present invention can accurately examine the antibody and the antigen. That is, when it is agglutination or non-agglutination, one examining step can be completed, and when it is in the intermediate state between the agglutination and non-agglutination, the reaction is conducted again in the reaction container to confirm whether or not it is agglutination or non-agglutination. As a result, the examining accuracy can be improved.

What is claimed is:

1. A system for discriminating a precipitation pattern of particles, comprising:
   a transparent reaction container having a bottom inner surface, part of which is inclined at a predetermined angle and on which a precipitation pattern of particles to be examined is formed based on immunological agglutination;

a light source for illuminating the bottom inner surface of said reaction container;

a lens for projecting an image of the precipitation pattern formed on the bottom inner surface of said reaction container and composed of first, second and third image sections which correspond to the lowest, middle and highest regions of the precipitation pattern;

at least one first photodetecting element for detecting the first image section;

at least one second photodetecting element for detecting the second image section;

at least one third photodetecting element for detecting the third image section;

first generating means for generating a first detection signal which corresponds to a difference between output signals supplied from said first and third photodetecting elements respectively;

second generating means for generating a second detecting signal which corresponds to a difference between an output signal supplied from one of said first and third photodetecting elements and an output signal supplied from said second photodetecting element;

first comparing means for comparing the second detecting signal with a reference signal to generate a correction signal; and second comparing means for comparing both the first and second signals to the correction signal to discriminate the precipitation pattern.

2. A system according to claim 1, wherein the inclined surface of the bottom of said reaction container forms an angle of 25 to 30° with respect to a horizontal plane.

3. A system according to claim 1, wherein the bottom surface of said reaction container is conically shaped.

4. A system according to claim 1, wherein the bottom of said reaction container is conically shaped, the precipitation pattern image is substantially circular, and the first photodetecting element is provided with spot-shaped photodetecting surface, and the second and the third photodetecting elements are provided with ring-shaped photodetecting surfaces, respectively.

5. A system according to claim 1, wherein said first, second and third photodetecting elements comprise a single photodetecting element, a plurality of second photodetecting elements and a plurality of third photodetecting elements, and means for adding output signals from said second photodetecting elements, and means for adding output signals from said third photodetecting elements.

6. A system according to claim 5, wherein said first, second and third photodetecting elements are provided with spot-shaped photodetecting surfaces, respectively.

7. A system according to claim 6, wherein the bottom surface of said reaction container is conically shaped, and the precipitation pattern image is substantially circular.

8. A system according to claim 7, wherein the spot-shaped photodetecting surfaces are linearly arranged.

9. A system according to claim 7, wherein the spot-shaped photodetecting surface of said second and third photodetecting elements are arranged coaxially.

* * * * *